United States Patent [19]
Rasmusson et al.

[11] Patent Number: 5,163,965
[45] Date of Patent: Nov. 17, 1992

[54] PROSTHETIC ATTACHMENT DEVICE AND METHOD

[75] Inventors: James K. Rasmusson, Birmingham; Wendy A. Fischl, Clarkston, both of Mich.

[73] Assignee: Becker Orthopedic Appliance Company, Troy, Mich.

[21] Appl. No.: 737,120

[22] Filed: Jul. 29, 1991

[51] Int. Cl.⁵ ............................................. A61F 2/60
[52] U.S. Cl. ................................. 623/36; 623/57; 623/901; 264/274
[58] Field of Search .................. 623/32–38, 623/27, 57, 901; 264/274, 275

[56] References Cited

U.S. PATENT DOCUMENTS

| | | | |
|---|---|---|---|
| 2,944,846 | 7/1960 | Jones | 623/57 X |
| 4,134,159 | 1/1979 | Wilson | 623/35 X |
| 4,370,791 | 2/1983 | Wilson | 264/274 X |
| 5,013,325 | 5/1991 | Rennerfelt | 623/38 |

FOREIGN PATENT DOCUMENTS

| | | | |
|---|---|---|---|
| 2586555 | 3/1987 | France | 623/33 |
| 2069847 | 9/1981 | United Kingdom | 623/32 |
| 2162069 | 1/1986 | United Kingdom | 623/36 |

OTHER PUBLICATIONS

Catalog, Pel Supply Co., pp. 75-76.
Catalog, Rehabilitation Technical Components, Inc., Catalog No. 040-1000-50.

*Primary Examiner*—Randall L. Green
*Assistant Examiner*—D. Willse
*Attorney, Agent, or Firm*—Jenner & Block

[57] ABSTRACT

Attachment devices for joining endoskeletal, prosthesis to prosthetic sockets on a person's stump are disclosed. The couplers have a peripheral notch on their side surfaces which define a void into which material can be molded to effectively secure the coupler to the socket. A depression is provided in the top surface of the device to facilitate fitting to a prosthetic socket.

31 Claims, 3 Drawing Sheets

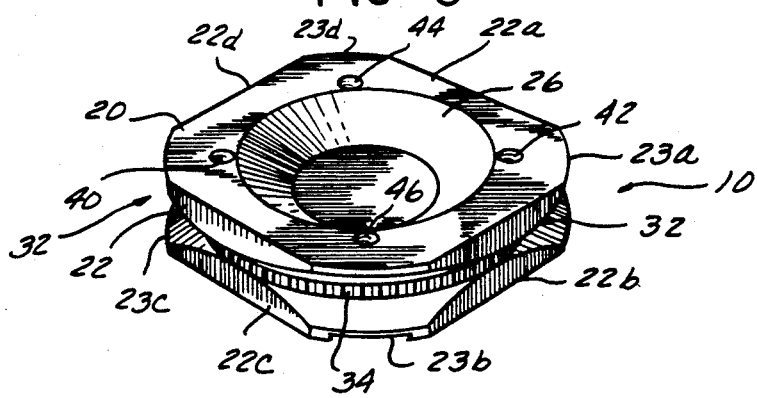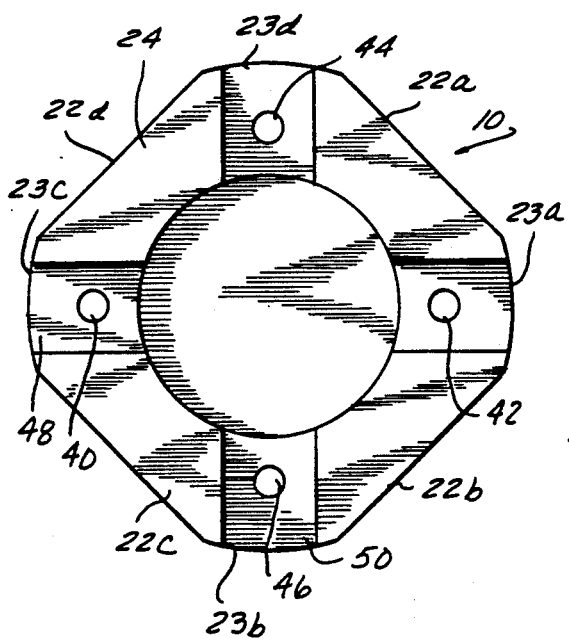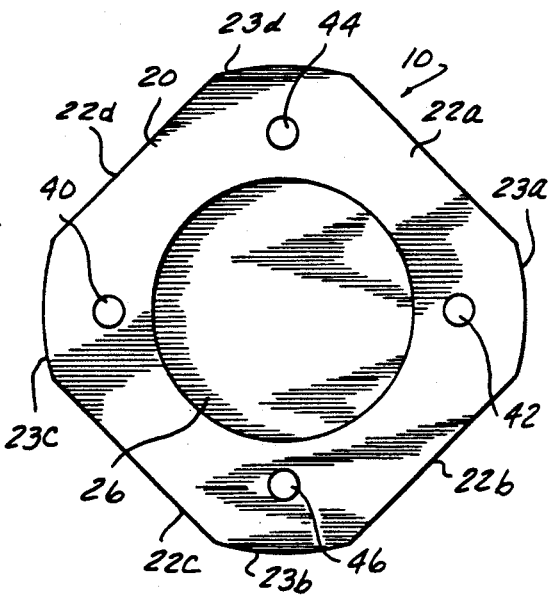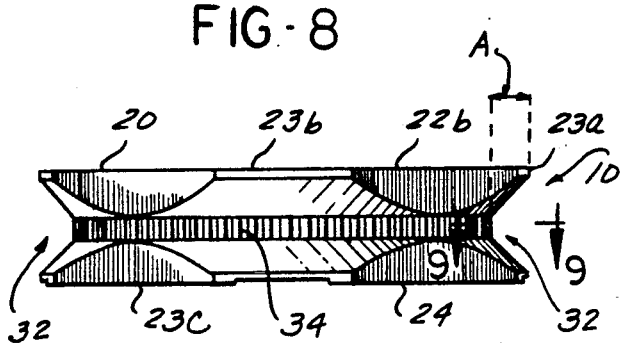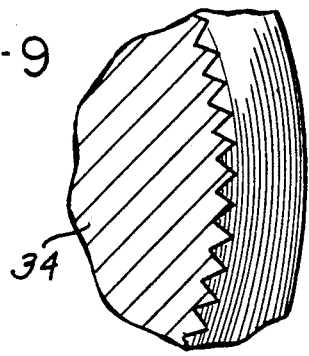

FIG.-10
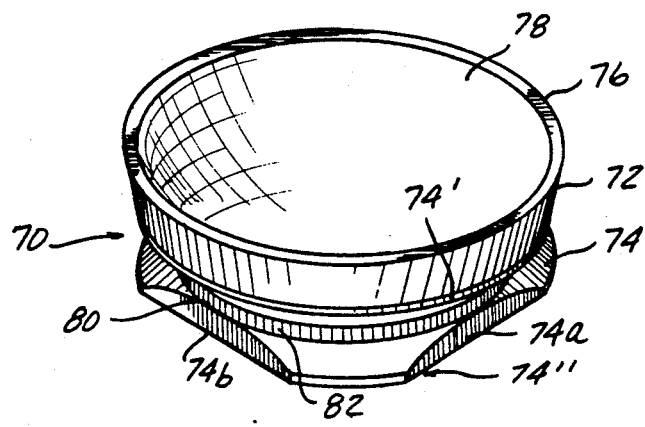
FIG.-11
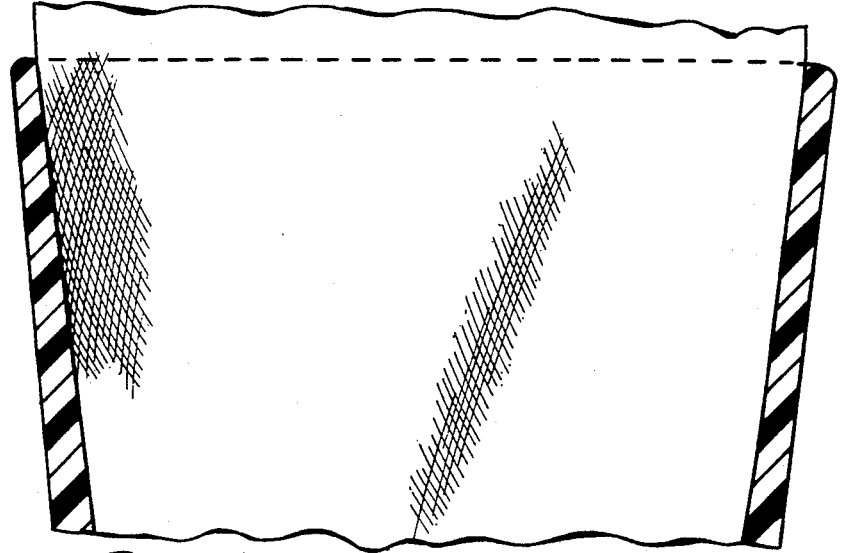
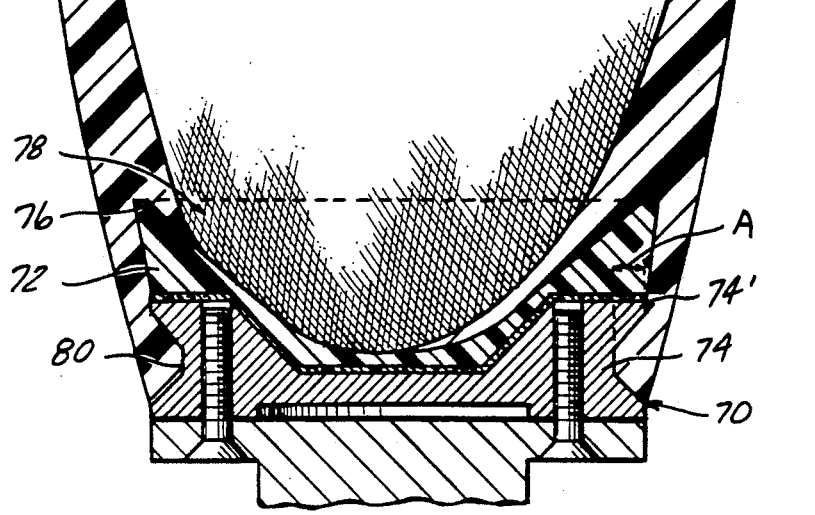

PROSTHETIC ATTACHMENT DEVICE AND METHOD

TECHNICAL FIELD

This invention generally relates to the field of artificial limbs. More particularly, this invention relates to the attaching of an artificial limb or prosthetic device to a patient's stump socket.

BACKGROUND OF THE INVENTION

In the context of the present invention, a prosthesis is a manufactured device for replacing a missing part of a body, such as a limb or portion thereof. There are two basic types of prosthesis: exoskeletal and endoskeletal. An exoskeletal prosthesis, also called a crustacial prosthesis, is supported by a rigid outer shell. An endoskeletal prosthesis is supported by internal support members. That is, structural support is provided by members inside the prosthesis.

Endoskeletal protheses are rapidly growing in popularity. A need exists for a reliable and efficient device and method that does not require a high degree of specialized equipment and/or skill for attaching an endoskeletal prosthesis to a patient, such as to the patient's molded stump socket or bandage wrap stump socket.

A stump socket is typically made by molding material around a person's stump or a positive model of the stump thereby forming a prosthetic socket or stump socket that can be worn by a patient over the stump and a remaining portion of a person's limb. Once the socket has been manufactured, or while it is being manufactured, it is secured to an attachment device which is then mounted to the endoskeletal prosthesis, typically by molding a portion of the stump socket to the attachment device.

A bandage wrap stump socket is made by applying activated plaster or resin bandage material over a person's stump and adjacent residual limb after an amputation operation.

Two types of attachment devices are known in the prior art. One type of attachment device that is commonly utilized to mount the stump socket to the prosthesis, shown in FIG. 3, is a flat metal disc or plate 30, typically having four threaded holes. The metal disc or plate can be round or square. Typically, the prosthesis is bolted or secured by other suitable threaded fasteners to the coupler thereby providing an artificial limb for the patient to wear. In order for the metal disc to be more securely attached to the stump socket, thermoplastic or other suitable material is molded around the periphery of the metal plate and around the bottom side of the metal plate opposite the side at which the persons' stump is to be located. Otherwise, the socket would detach more easily during use especially if a thermoforming resin is used. Thermoforming resins, such as polypropylene are especially difficult to use because such resins shrink when cooled. This bottom side is the same side to which the prosthetic device attaches to the plate by means of threaded fasteners. Thus, there is a layer of thermoplastic material between the plate and the end of the prosthetic device through which the fasteners pass to secure the prosthetic device to the plate. Since plastic material is sandwiched between the metal attachment plate and portion of the prosthesis attached to the plate, which is usually also metal, the plastic typically will deform under load and causes the socket to become loose. Some metal plate attachment devices have knurls on their side surfaces to facilitate attachment of the plate to the thermoplastic of the socket, but it is still necessary for the thermoplastic to be formed around the bottom side of the plate.

The flat metal plate attachment device poses an additional problem. During fitting to a patient, it is difficult to locate the metal plate on either the stump or on a positive model of the stump in the desired orientation. Since stumps and therefore the stump models typically have rounded ends, the flat metal plate device must be maintained in the desired orientation on the rounded end of the stump and/or stump model during the placing and at least partial curing of the moldable material around the metal plate and the socket. This balancing of the metal plate device is difficult, time consuming and skill intensive.

The second known attachment device is a wood attachment block 27, illustrated in FIG. 4. In order to fit the block to a patient, top surface 28 of wooden block 27 is carved out to fit the contours of the patient's stump socket. Typically, this requires a high level of skill and is time intensive. In addition, to secure the contoured wood block to the stump socket, thermosetting resins are typically used for the required adhesion to wood. These resins are difficult to work with because they are generally liquid and also are time consuming and toxic. Thus, not only is the fitting of wooden attachment blocks skill and time intensive, but it typically requires the use of toxic material to attach the block to the stump socket. Thermoforming resins are generally not suitable for wood attachment blocks.

Therefore, a need exists for a prosthetic attachment device that securely attaches to a prosthetic socket or stump socket without the aforementioned limitations. In addition, a need exists to reduce the amount of time and skill needed to attach an endoskeletal prosthesis to a prosthetic or stump socket. A need exists that permits use of thermoforming resins (especially polypropylene and transparent resins) without extending the resin over the bottom of the attachment device.

SUMMARY OF THE INVENTION

The prosthetic attachment device of the present invention couples an endoskeletal prosthesis to a prosthetic socket or stump socket. The prosthetic attachment device has a bottom surface and a top surface wherein the top surface has a depression designed to accept the end of a stump. A side surface extends between the top and bottom surfaces and has a peripheral undercut notch. This undercut notch defines a volume between the two surfaces into which material and/or adhesive can be molded to secure the coupler to the socket. Optionally, the undercut notch defines an inner surface which has a plurality of knurls. The undercut needs to be sufficiently deep to permit a good mechanical attachment of the molding material (which generally can be either a thermoforming or a thermosetting resin) to the prosthetic attachment device. Typically, an undercut depth of about 0.1 inch or more as measured from the top peripheral edge of the attachment device is sufficient. The undercut depth may be 0.125 inches or more.

The attachment device can be formed in one piece, such as a metal casting, or can comprise two elements, such as rigid top and bottom elements. The top element defines the top surface and the depression for accommodating the end of the stump. It is preferably generally disc-shaped and preferably composed of a layer of wooden like material rigidly secured to the bottom element. The bottom element which is preferably also generally disc-shaped and can define the undercut notch and may be metal.

An embodiment of the attachment device of the present invention is especially suitable in a post-operative setting where an amputation has recently been performed. The attachment device includes an attachment body having top and bottom surfaces and an undercut notch as previously described. In addition, the bottom surface has a plurality of grooves for the ends of attachment straps to be secured therein. The other ends of the attachment straps are secured to the patient such as by embedding them in a plaster cast that extends around the patient's remaining limb portion. A similar attachment device is especially suitable (preferably without grooves in the bottom) for use in a permanent attachment with thermoforming or thermosetting resins.

Another embodiment of the present invention comprises an artificial limb incorporating either of the attachment devices previously described. The artificial limb includes an endoskeletal prosthesis, a prosthetic socket and a prosthetic attachment device that joins the endoskeletal prosthesis to the prosthetic socket. The attachment device in this embodiment has a bottom surface and a top surface wherein the top surface has a depression which is designed to accept the end of a stump socket. Between the top and bottom surfaces of the attachment device extends a side surface which has a peripheral undercut notch as previously described. The undercut notch should generally be at least about 0.1 inch in depth and defines a volume between the two surfaces into which material can be molded to secure the coupler to the socket. Optionally, the undercut notch defines an inner surface which has a plurality of knurls.

The artificial limb of the present invention can further comprise suitable attachment structure to secure the artificial limb to a person and/or animal, such as straps or other structure.

The present invention further includes a method of making an artificial limb utilizing an attachment device in accordance with the present invention. The method includes the step of molding material about a stump and/or model of a stump to make a prosthetic socket or otherwise providing a prosthetic socket. Molding material or adhesive placed on the material is molded into a notch on the side surface of the attachment device to thereby secure the coupler to the prosthetic socket. The notch defines a volume between the two surfaces into which the material is molded to secure the coupler to the socket. In this embodiment of the invention, the coupler has both a bottom surface and a top surface having a depression designed to accept a stump. Finally, the endoskeletal prosthesis is fixedly secured to the bottom surface of the coupler. The prosthetic socket can be composed of the same material as the material that is molded to the attachment device.

For the purposes of the present invention, it is understood that a stump can be either a human and/or animal stump or a positive model of a human and/or animal stump.

BRIEF DESCRIPTION OF THE DRAWINGS

FIG. 5 is a perspective view of the prosthetic attachment device shown in FIG. 1;

FIG. 6 is a bottom view of the prosthetic attachment device in FIG. 5;

FIG. 7 is a top view of the prosthetic attachment device in FIG. 5;

FIG. 8 is a side view of the prosthetic attachment device in FIG. 5;

FIG. 9 is a cross-sectional view of the prosthetic attachment device in FIG. 8 taken along lines 9—9;

FIG. 10 is a perspective view of another prosthetic attachment device in accordance with the present invention; and FIG. 11 is a cross-sectional view of the prosthetic attachment device of FIG. 10 and an attached prosthetic socket.

DETAILED DESCRIPTION OF THE PRESENT INVENTION

Two basic embodiments will now be described. The first is a temporary post-operative attachment device, especially useful where a recent amputation has been made, leaving the stump. The second embodiment is a permanent prosthetic attachment device.

Figure 1:
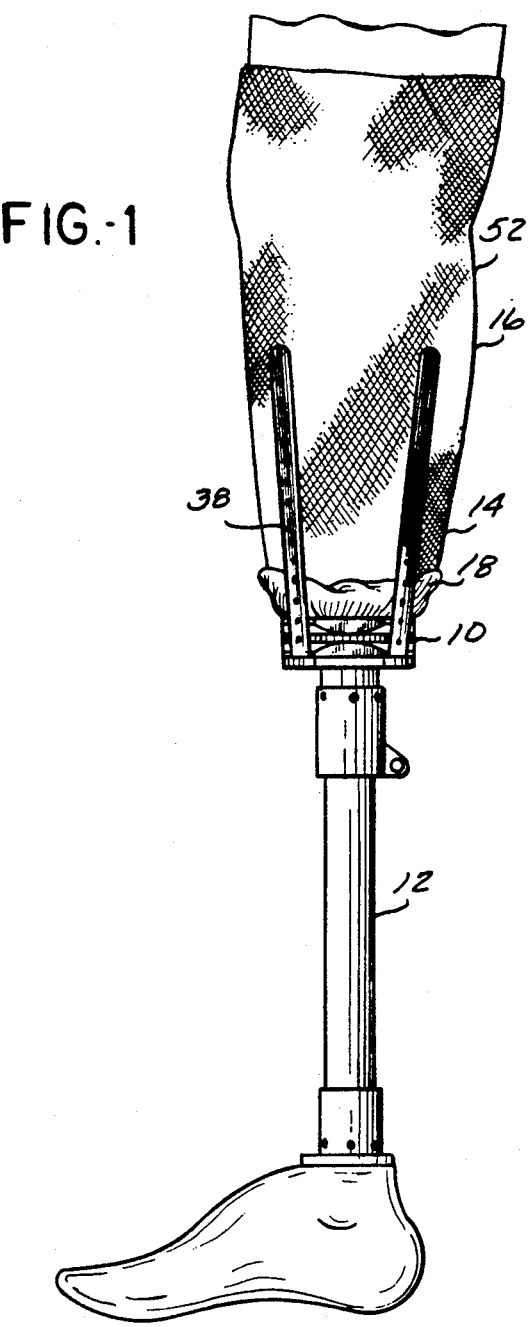
FIG. 1 is a perspective view of the present invention illustrating the prosthetic attachment device before plaster bandage has been applied to the socket.
Figure 2:
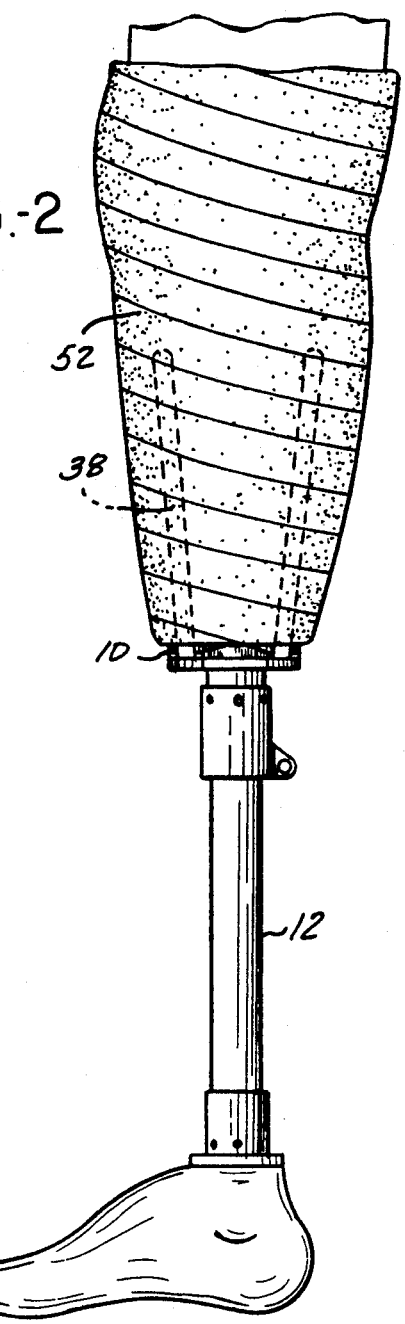
FIG. 2 is another perspective view of the embodiment of FIG. 1 after plaster bandage has been applied to the socket.

FIGS. 1 and 2 show side elevation views of an embodiment of the present invention in various stages of attachment. In this embodiment of the invention, a prosthetic attachment device 10 secures an endoskeletal prosthetic device 12 to a prosthetic socket 14 in a post-operative setting.

Socket 14 is manufactured by initially placing a stump sock 16 on a patient. After stump sock 14 is applied, a layer of padding 18 is applied to the distal end of the stump. Once stump sock 16 and padding 18 are in place, prosthetic attachment device 10 is placed over padding 18.

Turning to FIGS. 5, 6 and 7, prosthetic attachment device 10 is shown in greater detail. Prosthetic attachment device 10 comprises a top surface 20, side surface 22 and a bottom surface 24. As best seen in FIGS. 5 and 7, top surface 20 of prosthetic attachment device 10 has a depression 26 which is designed to accept a stump. Peripheral notch 32 of the present invention of prosthetic attachment device 10 defines a volume into which material is molded to secure prosthetic attachment device 10 to socket 14. The depth (inwardly extending lateral distance) of notch 32 as illustrated by reference letter A in FIG. 8 is about 0.25 inches as measured from the top peripheral edge of top surface 20 along corner 23a of prosthetic attachment device 10. Preferably, the notch depth will be at least about 0.1 inches. The depth can be greater than 0.125 inches.

The material molded into notch 32 can be the material that the socket is composed of or it can be an adhesive securing socket 14 to prosthetic attachment device 10. For example, the material can comprise of a variety of substances such as thermoset resin plastics, thermoform sheet plastic and even plaster bandage.

Figure 3:
FIG. 3 is a perspective view of a prior art metal plate attaching device.
Figure 4:
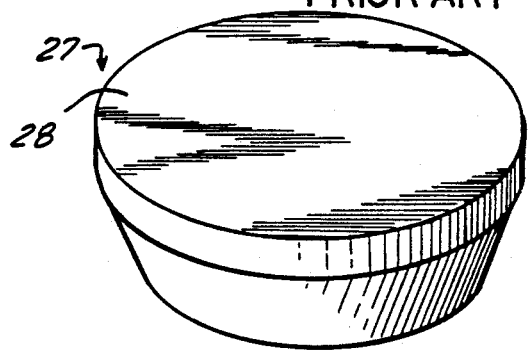
FIG. 4 is a perspective view of a prior art wood block attachment device.

To increase the bonding of the material to prosthetic attachment device 10, notch 32 can include a plurality of knurls 34 or other small surface depressions which provide the material with a greater surface area to adhere, as illustrated in FIGS. 5 and 8-9. Although prior art metal plate coupler 30 has a knurled side surface 38, a comparison of the coupler of FIG. 3 with the coupler of the present invention as seen in FIGS. 5, 8 and 9 reveals that knurled side surface 37 does not present any undercut notch or similar structure extending inwardly from the top peripheral edge of top surface of coupler 30 of any appreciable distance.

As illustrated in FIGS. 5-8, prosthetic attachment device 10 is generally disc-shaped with four truncated sides 22a, 22b, 22c and 22d. Knurls 34 extend around the periphery of side 22. Undercut peripheral notch 32 is located between top and bottom surfaces 20 and 24 along corners 23a, 23b, 23c and 23d of side surface 22 which are located between each of truncated sides 22a-d.

In addition to notch 32, a plurality of straps 38 are provided to further secure prosthetic attachment device 10 to socket 14. At one end, straps 38 are secured to threaded apertures 40, 42, 44, and 46 by any suitable means such as bolts which can fixedly secure each strap 38 to its respective aperture 40, 42, 44, and 46. Apertures 40, 42, 44 and 46 extend from bottom surface to top surface and are found in one of two intersecting grooves 48 and 50. Apertures 40 and 42 are located in groove 48 and apertures 44 and 46 and are located in groove 50.

In this embodiment of the present invention, straps 38 are initially bent to conform to the shape of socket 14. Once they are bent into shape, prosthetic attachment device 10 is removed from socket 14. Upon removal, a plaster bandage 52 is applied to socket. While plaster bandage 52 is still soft, prosthetic attachment device 10 is reapplied and straps 38 are pressed into the first layer of wet plaster bandage 52. After pressing straps 38 into the plaster bandage 52, additional layers of plaster forming part of plaster bandage 54 are applied, covering straps 38 thereby securing the straps 38 to socket 14.

In another embodiment of the present invention similar to that described with respect to FIGS. 1-2 and 5-9, a permanent attachment device similar to post-operative attachment device 10 but lacking grooves 48 and 50 is provided, In use, such an attachment device is placed onto the distal end of a positive model of a stump. In this embodiment of the present invention, the attachment device, instead of being secured to socket by straps 38, is directly molded to socket. The material comprising socket is molded into a peripheral notch and contacted with knurls. As was the case with the first embodiment of the present invention, the material molded into the notch can be the actual material of which the socket is composed or it can be any suitable adhesive capable of bonding the socket to the attachment device. If the material is thermoset resin, a layer of reinforcing fabric such as nylon, fiberglass stocking, fiberglass matting and strips of woven carbon graphite must be applied. Then, the thermoset resin is impregnated on the reinforcing fabric (not illustrated in the drawings). Attachment device 10 with grooves 48 could also be used as a permanent attachment device.

FIGS. 10 and 11 illustrate another embodiment of the present invention. In this embodiment of the invention, an attachment device 70 is composed of a rigid top element 72 and a bottom element 74 which is preferably made of anodized aluminum. Top element 72 is generally disc-shaped and composed of rigid foam preferably having properties, such as strength, hardness and machinability similar to that of wood. Any suitable rigid foam having such properties can be utilized, including, for example, polyurethane, polystyrene, polypropylene, and polyethylene. In addition, top element 72 comprises a top surface 76 having a depression 78 designed to accept a stump 79. Depression 78 can be customized to fit stump 79 because additional uncured foam or other moldable material can be poured into top element 72 thereby allowing top element 72 to conform to the shape of the stump. The molten foam is easily shaped and readily conforms to the shape of stump 79. An especially preferred foam is a urethane foam from Stepan Chemical Co. of Northfield, Ill. sold under the name Stepanfoam, which is a two-part rigid urethane water blown foam of eight pounds per cubic foot freerise density, preferably used at a packed density of about 15 pounds per cubic foot.

Preferably, the surface of depression 78 is coated with acrylic resin, especially when a hygroscopic urethane is used for top element 72. The treatment with acrylic resin seals the surface of depression 78 and provides a better bonding surface for attachment of stump socket 82. A preferred acrylic resin is Ortho Cryl ® sealing resin from Otto Bock Orthopedic Co., having an office in Minneapolis, Minn.

Bottom element 74 of attachment device 70 can be rigidly secured to top element 72 before or after top element 72 is prepared for application to the stump. Bottom element 74 is secured to the top element 72 by a layer of any suitable adhesive which will adhere elements 72 and 74. A preferred adhesive is a polymer adhesive, sold under the trademark Chemlok 210 and manufactured by Lord Corp. of Erie, Pa. Chemlok 210 is a proprietary mixture of polymers, curatives and dye dissolved in a blend of three solvents: methylethylketone, xylene and Dowanol BC300. In this embodiment, bottom element 74 which is similar to attachment device 10 with top element 72 attached thereto, except that portion 74' of bottom element 74 that corresponds to the top half of attachment device 10 does not have truncated sides. This configuration provides an additional undercut volume for adhesive moldable material to be located therein, thereby providing a stronger bond. The bottom portion 74" of bottom element 74 does have four identical truncated sides (of which only two are illustrated in FIG. 10, sides 74a and 74b) also has a peripheral notch 80 which defines a volume into which material is molded to secure attachment device 70 to socket 82. The material molded into notch can be the actual material of which socket 82 is composed or it can be any suitable adhesive as discussed in conjunction with the first and second embodiments of the present invention which can secure socket 82 to attachment device 70.

To increase the bonding of the material to attachment device 70, notch 80, includes a plurality of knurls 82 which provide the material with a greater surface area to adhere to. Knurls 82 provide a rough friction-laden surface, which enhances the bonding of the material with attachment device 70 by providing a surface upon which the material can attach and adhere to.

In the embodiments illustrated in FIGS. 1-2 and 5-11, notches 32 and 80 extend inwardly a maximum of about 0.125 inches (dimension A in FIGS. 8 and 11).

The following is a description of utilizing attachment devices 10 and 70. Preferably, for utilizing attachment device 10 in a temporary post-operative setting, straps 38 are secured to threaded apertures 40, 42, 44 and 46.

Straps 38 are then contoured to the patient's residual limb. Straps 38 are then secured between layers of a plaster and/or resin bandage.

Attachment device 10 (preferably without grooves 48) is utilized as follows for a permanent attachment with either thermosetting (wet) plastic laminate or a thermoforming plastic. Preferably, a positive model of the patient's stump is obtained. The positive model of the stump is secured in a vise or other fixture, distal end up. If the socket is to be a soft socket, the liner will have been fabricated and in place on the stump model. The attachment device is then placed onto the distal end of the model in the desired alignment. The attachment device has a conical indentation, which provides proper alignment that is easy and self-centering. The attachment device can be immobilized in the desired orientation by applying wet plaster to the conical depression. Alternatively, the attachment device can be nailed or otherwise secured to the positive model of the patient's stump. Nailing requires the drilling of a small hole through the center of the attachment device. The plastic material for the socket, whether sheet or resin material, is then applied over the model and sides of the attachment device, which can be done by well-known vacuum molding techniques. When the plaster sets, it is removed from the conical depression with the positive stump model. Prior to placing the patient's stump into the stump socket, a void filling material (such as RTV (room temperature vulcanization) foam) is poured into the bottom of the stump socket, including the conical depression to fill any voids between the patient's stump and distal aspect of the stump socket (the top of the attachment device).

Alternatively, attachment device 70, or an attachment device similar to attachment device 10 but lacking grooves 48 and 50 for straps can be attached as follows. The positive model of the patient's stump is secured in a vertical alignment jig, distal end down. The attachment device is secured to the desired endoskeletal prosthetic system. Thereafter, the prosthetic endoskeletal system is secured to the foot plate of the jig. Proper alignment is then established with the distal end of the stump model being directly over the conical depression of the attachment device. Plaster or other similar material is then poured into the conical depression and the positive stump model is then lowered into contact with the plaster, forcing some of the plaster out of the conical depression. As the plaster begins to firm up, it can be smoothed and contoured as desired. After the plaster has set up, the prosthetic endoskeletal system is removed from the attachment device. The attachment device is then ready to have the plastic in either sheet or resin form, for example, applied over the positive stump model and attachment device as previously described. Thereafter, the model and plaster is removed and filling material utilized as previously described.

Attachment device 70 should be used with a thermosetting (wet) plastic lamination material. The installation can be the same as described previously for attachment device 70. Use of attachment device 70 with a thermoforming plastic is generally not desirable since the adhesive securing top element 72 to bottom element 74 can fail with thermoforming plastic. In addition, urethane can be added to depression 78 of top element 72 to allow top element 72 to conform to the shape of the positive stump model.

EXAMPLE 1

A test was conducted to determine the strength of the joint formed between a prosthetic socket and an attachment device in accordance with the present invention. The, test simulated the maximum forces on a prosthesis which occurs during the "rollover" segment of a person's gait cycle.

In this test, the bottom flat portion of an attachment device identical to attachment device 10 illustrated in FIG. 5 (but without grooves 48) was attached to an upstanding vertical wall. A polypropylene prosthetic socket was formed over the sides of the attachment device, similar to that illustrated in FIG. 11. The prosthetic socket was made of 0.1875 inch thick polypropylene. No plastic covered the bottom of the attachment device. The plastic extending over the sides of the attachment device was flush with the bottom portion of the device. During fabrication of the prosthetic socket, the molten polypropylene was not forced into the undercuts of the attachment device but was merely allowed to draw into the undercut region by vacuum.

During the test, an upward vertical force is applied through a sling that passes underneath the prosthetic socket near the end of the socket opposite the end that is attached to the attachment device. The force is progressively increased until failure occurs. For the 0.1875 inch thick polypropylene, at a force of 151 foot pounds, the plastic failed at a point just above the attachment device. There was no separation of the polypropylene from the attachment device. Rather, material of the prosthetic socket failed apart from the area that is attached to the attachment device.

EXAMPLE 2

A test similar to that described in Example 1 was performed except that 0.1875 inch thick thermoset plastic (Bock 5 R1 from Bock Orthopedic) was utilized. The thermoset plastic was an acrylic resin saturated into nylon and fiberglass that was about 0.1875 inches thick.

Failure occurred at a location similar to that described with respect to Example 1 at a force of 450 foot pounds.

It should be apparent that a wide range of changes and modifications can be made to the embodiments of the present invention described above. It is, therefore, intended that the foregoing detailed description be regarded as illustrative rather than limiting, and it be understood that it is the following claims, including all equivalents, which are intended to define this invention.

We claim:

1. An attachment device for attaching an endoskeletal prosthesis to a prosthetic socket that can be worn over the end of a person's stump, the device comprising a rigid body having a bottom surface having a bottom peripheral edge, a top surface having a top peripheral edge and having a depression in the top surface for accepting the bottom portion of the stump, the device having a side surface extending between said bottom surface and said top surface, wherein the side surface has an inwardly extending portion that has a depth of at least about 0.1 inch measured from the top peripheral edge, said portion located between the top and bottom peripheral edges, and said inwardly extending portion defining a volume under the top peripheral edge into which material can be molded to secure said device to said socket and means for permitting attachment of the prosthesis to the bottom surface of the rigid body.

2. The device of claim 1 wherein said side surface that extends inwardly comprises a peripheral undercut notch.

3. The device of claim 2 wherein a portion of said undercut notch has a maximum depth of at least about 0.125 inches inwardly from the top and bottom peripheral edges.

4. The device of claim 2 wherein said undercut notch has a V-shaped cross-section.

5. The device of claim 2 wherein said rigid body is composed of rigid top and bottom elements, said top element defining said top surface and said depression and composed of a layer of wooden-like material rigidly secured to the bottom element, said bottom element having said undercut notch.

6. The device of claim 5 wherein said bottom element is metal and the top element is adhesively secured thereto.

7. The device of claim 5 wherein said bottom element is disc-shaped and said top element is disc-shaped and composed of polymer foam adhesively secured to said bottom element.

8. The device of claim 7 further comprising a layer of adhesive between said top and bottom elements for securing said top element to said bottom element.

9. The device of claim 8 wherein said rigid foam is selected from the group consisting of polyurethane, polystyrene, polyethylene, and polypropylene.

10. The device of claim 5 wherein said top element is composed of rigid foam.

11. The device of claim 2 wherein said undercut notch extends around the circumference of said side surface.

12. The device of claim 1 wherein said means for permitting attachment to the prosthesis comprises four spaced apart holes extending through said bottom surface, said bottom surface having four spaced apart grooves each extending inwardly from the bottom peripheral edge over a different one of said holes.

13. The device of claim 12 wherein each of said holes is located adjacent the outer bottom peripheral edge of said bottom surface, said device further comprising four straps, each strap having one end disposed within one of said grooves and secured to the bottom through said holes.

14. An artificial limb comprising:
an endoskeletal prosthesis;
a prosthetic socket having a lower portion of molding material;
a device joining said endoskeletal prosthesis to said prosthetic socket, said device comprising a rigid body having a bottom surface having a bottom peripheral edge, a top surface having a top peripheral edge and having a depression in the top surface for accepting the bottom portion of the stump, the device having a side surface extending between said bottom surface and said top surface, wherein the side surface has an inwardly extending portion that extends inwardly at least about 0.1 inch from the top peripheral edge between the top and bottom peripheral edges, said inwardly extending portion defining a volume under the top peripheral edge into which said molding material of prosthetic socket can be molded to secure said device to said socket; and
means for attaching said prosthesis to said bottom surface of the rigid body.

15. The artificial limb of claim 14 wherein said side surface that extends inwardly comprises a peripheral undercut notch.

16. The artificial limb of claim 15 wherein a portion of said undercut notch extends at least about 0.125 inches inwardly from the top and bottom peripheral edges.

17. The artificial limb of claim 15 wherein said undercut notch has a V-shaped cross-section.

18. The artificial limb of claim 17 wherein said device is composed of rigid top and bottom elements, said top element defining said top surface and said depression and composed of a layer of wooden-like material rigidly secured to the bottom element, said bottom element having said undercut notch.

19. The artificial limb of claim 18 wherein said bottom element is metal and the top element is adhesively secured thereto.

20. The artificial limb of claim 19 wherein said bottom element is disc-shaped and said top element is disc-shaped and composed of polymer foam adhesively secured to said bottom element.

21. The artificial limb of claim 20 further comprising a layer of adhesive between said top and bottom elements for securing said top element to said bottom element.

22. The artificial limb of claim 19 wherein said top element is composed of rigid foam.

23. The artificial limb of claim 22, wherein said rigid foam is selected from the group consisting of polyurethane, polystyrene, polyethylene, and polypropylene.

24. The artificial limb of claim 15 wherein said undercut notch extends around the circumference of said side of said device.

25. The artificial limb of claim 14 wherein said means for attaching said prosthesis comprises four spaced apart holes extending through said bottom surface, said bottom surface having four spaced apart grooves each extending inwardly from the bottom peripheral edge over a different one of said holes.

26. The artificial limb of claim 25 wherein each of said holes is located adjacent the outer bottom peripheral edge of said bottom surface, said device further comprising four straps, each strap having one end disposed within one of said grooves and secured to the bottom through said holes.

27. The artificial limb of claim 14 further comprising securing means to secure said artificial limb to a human.

28. A method of making a prothesis for attachment to a person's stump, comprising the steps of:
(a) preparing a positive model of the stump, said model having a distal end;
(b) providing an attachment device comprising a rigid body having a bottom surface having a bottom peripheral edge, a top surface having a top peripheral edge and having a depression in the top surface for accepting the bottom portion of the stump, the device having a side surface extending between said bottom surface and said top surface, wherein the side surface has an inwardly extending portion that extends inwardly at least about 0.1 inch from the top peripheral edge between the top and bottom peripheral edges, said inwardly extending portion defining a volume under the top peripheral edge into which molding material can be molded;
(c) placing said attachment device on the distal end of said model so that the depression on the top surface of said attachment device engages the distal end of said model;

(d) applying molding material over said positive model and the sides of said attachment device;

(e) allowing said molding material to cure, thereby forming a stump socket; and (f) removing said positive model from said stump socket.

29. The method of claim 1 further comprising the steps of:

pouring a second molding material in said depression of said attachment device prior to placing said attachment device on said distal end of said model;

forcing a portion of said second molding material out of said depression after said attachment device is placed on said model; and allowing said second molding material to cure before applying said molding material.

30. The method of claim 1 further comprising the steps of:

attaching an endoskeletal member to the bottom surface of said attachment device;

aligning said attachment device after placing said attachment device on said model so that said endoskeletal system is in a desired orientation relative to said model;

immobilizing said attachment device relative to said model after said attachment device is so aligned; and removing said endoskeletal system after said attachment device is aligned and before said molding material is applied.

31. The method of claim 1 further comprising the steps of:

after said model is removed from said stump socket, filling the distal end of said stump socket with a void filling material; and placing the person's stump in said stump socket for engagement with the distal end of said stump socket.

* * * * *

UNITED STATES PATENT AND TRADEMARK OFFICE
CERTIFICATE OF CORRECTION

PATENT NO. : 5,163,965
DATED : November 17, 1992
INVENTOR(S) : James K. Rasmusson et al.

It is certified that error appears in the above-identified patent and that said Letters Patent is hereby corrected as shown below:

Column 1, line 67, before "causes" delete the comma ",".

Column 4, line 55, "0.25" should read --0.125--.

Column 5, line 44, after "provided" delete the comma "," and insert therefor a period --.--.

Column 6, line 59, after "surface" delete the comma ",".

Column 8, line 6, after "The" delete the comma ",".

Column 10, line 29, after "claim 22" delete the comma ",".

Column 11, line 9, "claim 1" should read --claim 28--; and line 20, "claim 1" should read --claim 28--.

Column 12, line 13, "claim 1" should read --claim 28--.

Signed and Sealed this

Fourteenth Day of December, 1993

*Attest:*

BRUCE LEHMAN

*Attesting Officer*     *Commissioner of Patents and Trademarks*